(12) United States Patent
Cecchi et al.

(10) Patent No.: US 8,271,414 B2
(45) Date of Patent: Sep. 18, 2012

(54) NETWORK CHARACTERIZATION, FEATURE EXTRACTION AND APPLICATION TO CLASSIFICATION

(75) Inventors: Guillermo Alberto Cecchi, New York, NY (US); Srinivas Ravi Viraraghava Iyengar, Mohegan Lake, NY (US); Avi Ma'ayan, New York, NY (US); Ravishankar Rao, Elmsford, NY (US); Gustavo Alejandro Stolovitzky, Riverdale, NY (US); John Michael Wagner, Plainville, CT (US)

(73) Assignees: International Business Machines Corporation, Armonk, NY (US); Mount Sinai School of Medicine of New York University, New York, NY (US)

( * ) Notice: Subject to any disclaimer, the term of this patent is extended or adjusted under 35 U.S.C. 154(b) by 601 days.

(21) Appl. No.: 12/508,791

(22) Filed: Jul. 24, 2009

(65) Prior Publication Data

US 2011/0022355 A1    Jan. 27, 2011

(51) Int. Cl.
  *G06F 17/00* (2006.01)
  *G06N 5/02* (2006.01)
(52) U.S. Cl. ........................................................ 706/46
(58) Field of Classification Search .................... 706/12, 706/45, 46
  See application file for complete search history.

(56) References Cited

U.S. PATENT DOCUMENTS

| 7,409,321 | B2 | 8/2008 | Repucci et al. |
| 2006/0173663 | A1 | 8/2006 | Langheier et al. |
| 2007/0036402 | A1 | 2/2007 | Cahill et al. |
| 2008/0030497 | A1 | 2/2008 | Hu et al. |
| 2008/0080775 | A1 | 4/2008 | Zabih et al. |
| 2009/0204554 | A1* | 8/2009 | Koren et al. ............... 706/12 |
| 2010/0153329 | A1* | 6/2010 | Ghosh et al. ............... 706/54 |

OTHER PUBLICATIONS

Sporns, Olaf et al.; "Organization, development and function of complex brain networks"; 2004; Elsevier; Trends in Cognitive Sciences, vol. 8, No. 9; pp. 418-425.*
Sporns, Olaf et al.; "Motifs in Brain Networks"; 2004; PLoS Biology, vol. 2, Issue 11; pp. 1910-1918.*
Reijneveld, Jaap C. et al.; "The application of graph theoretical analysis to complex networks in the brain"; 2007; Elsevier; Clinical Neurophysiology 118; pp. 2317-2331.*

(Continued)

*Primary Examiner* — Alan Chen
*Assistant Examiner* — Stanley K Hill
(74) *Attorney, Agent, or Firm* — Vazken Alexanian; Ryan, Mason & Lewis, LLP

(57) ABSTRACT

Methods, systems and apparatus for characterizing networks are presented. For example, a method of characterizing a network represented by a plurality of nodes and a plurality of edges is provided. The method may be implemented on a processor device and includes calculating, for example, by the processor device, a passthrough count of at least a portion of the network. The passthrough count includes a count of a number of passthroughs in the at least a portion of the network. A passthrough includes one of the plurality of nodes, a directed edge of the plurality of edges coupled to the one of the plurality of nodes, and another edge of the plurality of edges coupled to the one of the plurality of nodes. At most one of the directed edge and the other edge is directed towards the one of the plurality of nodes. At most one of the directed edge and the other edge is directed away from the one of the plurality of nodes.

29 Claims, 7 Drawing Sheets

OTHER PUBLICATIONS

Kaiser, Marcus; "A tutorial in connectome analysis: Topological and spatial features of brain networks"; 2011; Elsevier; NeuroImage 57; pp. 892-907.*

A. Ma'Ayan et al. "Ordered Cyclic Motifs Contribute to Dynamic Stability in Biological and Engineered Networks," Proceedings of the National Academy of Sciences of the United States of America, Dec. 2008, pp. 19235-19240, vol. 105, No. 49.

V.M. Eguiluz et al., "Scale-Free Brain Functional Networks," Physical Review Letters, Jan. 2005, 4 pages, vol. 94, No. 1.

V.N. Vapnik, "Informal Reasoning and Comments," The Nature of Statistical Learning Theory, 1999, Chapter 5, pp. 119-156.

J.R. Quinlan, "C4.5 Programs for Machine Learning," 1993, Chapters 1 and 2, pp. 1-27, vol. 16, No. 3.

* cited by examiner

PASSTHROUGH COUNT IS INCREMENTED BY 1

PASSTHROUGH COUNT IS INCREMENTED BY 1

PASSTHROUGH COUNT IS DECREMENTED BY 1

PASSTHROUGH COUNT IS DECREMENTED BY 1

PASSTHROUGH COUNT IS INCREMENTED BY 1

PASSTHROUGH COUNT IS INCREMENTED BY 1

PASSTHROUGH COUNT IS DECREMENTED BY 1

M = 0
H = 2
H_NORMAL = 1/3

M = 0
H = −6
H_NORMAL = −1

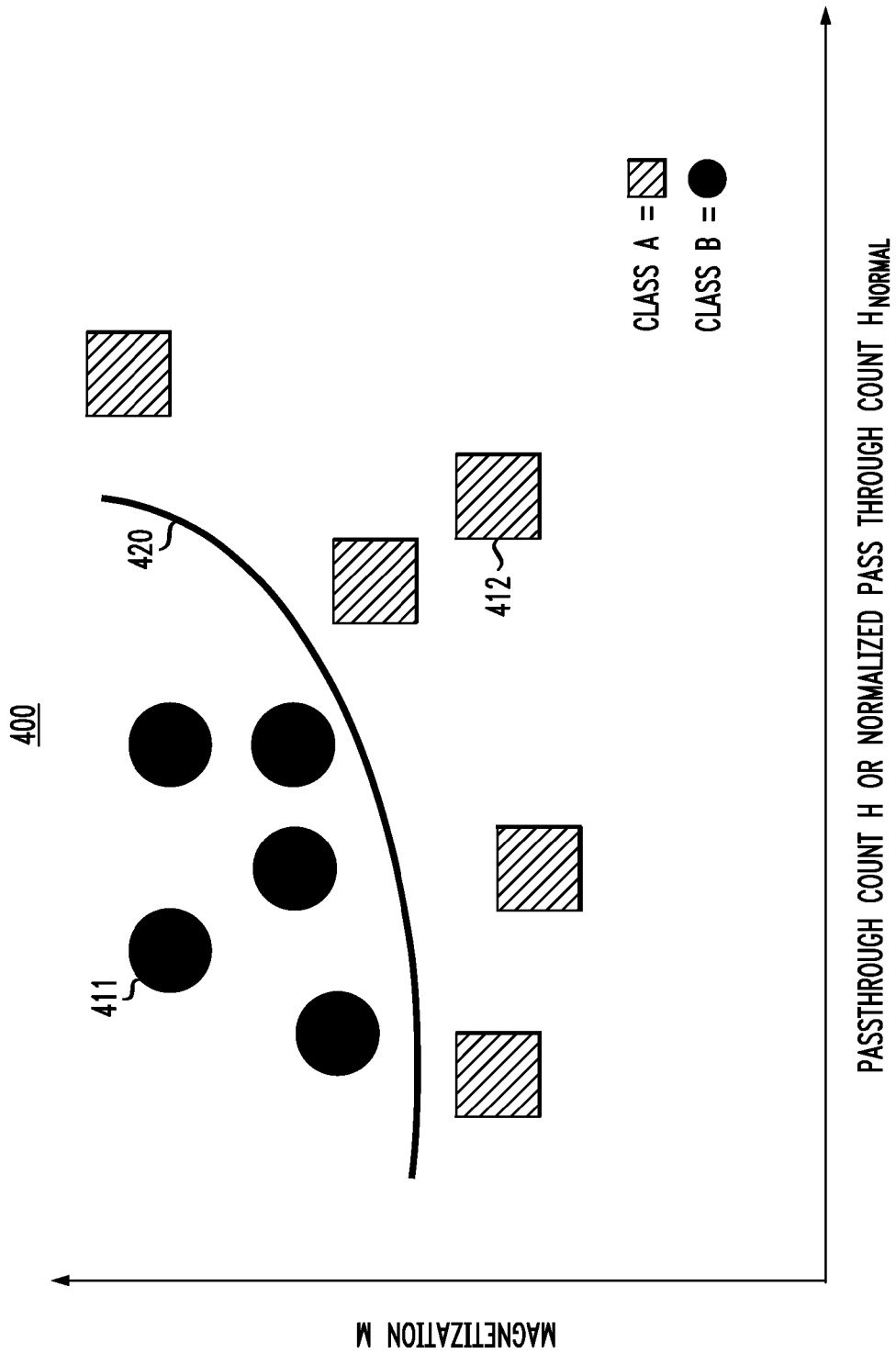

500

NETWORK CHARACTERIZATION, FEATURE EXTRACTION AND APPLICATION TO CLASSIFICATION

FIELD OF THE INVENTION

The present invention relates generally to network characterization. More particularly the invention relates to feature extraction from networks and application of feature extraction to classification tasks.

BACKGROUND OF THE INVENTION

Networks occur in a variety of domains, ranging from natural circuits in biological organisms to man-made circuits such as integrated circuits in semiconductor chips. At the simplest level, a network can be described in terms of its constituent elements, consisting of nodes and edges. A node may represent an object of interest, and edges may represent relationships between these objects. For instance, nodes could be cities, and edges could be the distance between cities that are connected by roads. In another context, nodes could represent voxels in a three-dimensional (3D) grid, and edges could connect two nodes that have correlated behavior. An edge may express a relationship between two nodes, and can be directed or undirected. A directed edge connecting two nodes A and B is typically denoted by an arrow, A→B, which can be read as "A leads to B", or "A causes B." In cases where such a directionality cannot be established, for instance where a causal (cause-effect) relationship cannot be determined, the edge are shown without any arrows, such as A-B, which is read as "A is related to B."

Various quantitative metrics have been proposed to characterize networks, such as the average degree of connectedness, or the average minimal distance of edges needed to connect all pairs of nodes. Other approaches to characterizing networks decompose networks into basic structural motifs, and examine the frequency of occurrence of these motifs in the overall network.

SUMMARY OF THE INVENTION

Principles of the invention provide, for example, methods, systems and apparatus for characterizing networks.

For example, in accordance with one embodiment of the invention, a method of characterizing a network represented by a plurality of nodes and a plurality of edges is provided. The method may be implemented on a processor device and includes calculating, for example, by the processor device, a passthrough count of at least a portion of the network. The passthrough count includes a count of a number of passthroughs in the at least a portion of the network. A passthrough includes one of the plurality of nodes, a directed edge of the plurality of edges coupled to the one of the plurality of nodes, and another edge of the plurality of edges coupled to the one of the plurality of nodes. At most one of the directed edge and the other edge is directed towards the one of the plurality of nodes. At most one of the directed edge and the other edge is directed away from the one of the plurality of nodes.

In accordance with another embodiment of the invention, a system for characterizing a network represented by a plurality of nodes and a plurality of edges is provided. The system comprises modules for implementing the above method for characterizing a network.

In accordance with yet another embodiment of the invention, apparatus for characterizing a network represented by a plurality of nodes and a plurality of edges is provided. The apparatus includes a memory and a processor device coupled to the memory. The apparatus is operative to perform the above method for characterizing a network.

In accordance with one more embodiment of the invention, a computer program product for characterizing a network represented by a plurality of nodes and a plurality of edges is provided. The computer program product comprises a computer readable storage medium having computer readable program code embodied therewith. The computer readable program code comprises computer readable program code configured to perform the above method for characterizing a network.

In accordance with an additional embodiment of the invention, a method, implemented on a processor device, of characterizing a network represented by a plurality of nodes and a plurality of edges is provided. The method includes calculating, for example, by the processor device, a magnetization indicator of a cycle of the network. The magnetization indicator includes a count of a number of edges of the cycle that point in a clockwise direction of the cycle and a count of a number of edges of the cycle that point in a counter-clockwise direction of the cycle.

Principles of the invention provide, for example, feature extraction from networks using topological measures of cycles, application of the feature extraction to classification processes, and discrimination between different subjects undergoing similar mental tasks or responding to similar stimuli.

BRIEF DESCRIPTION OF THE DRAWING

FIG. 4 illustrates a two-dimensional passthrough count-magnetization (H−|M|) feature plot, according to an embodiment of the present invention.

DETAILED DESCRIPTION OF THE INVENTION

Figure 1:
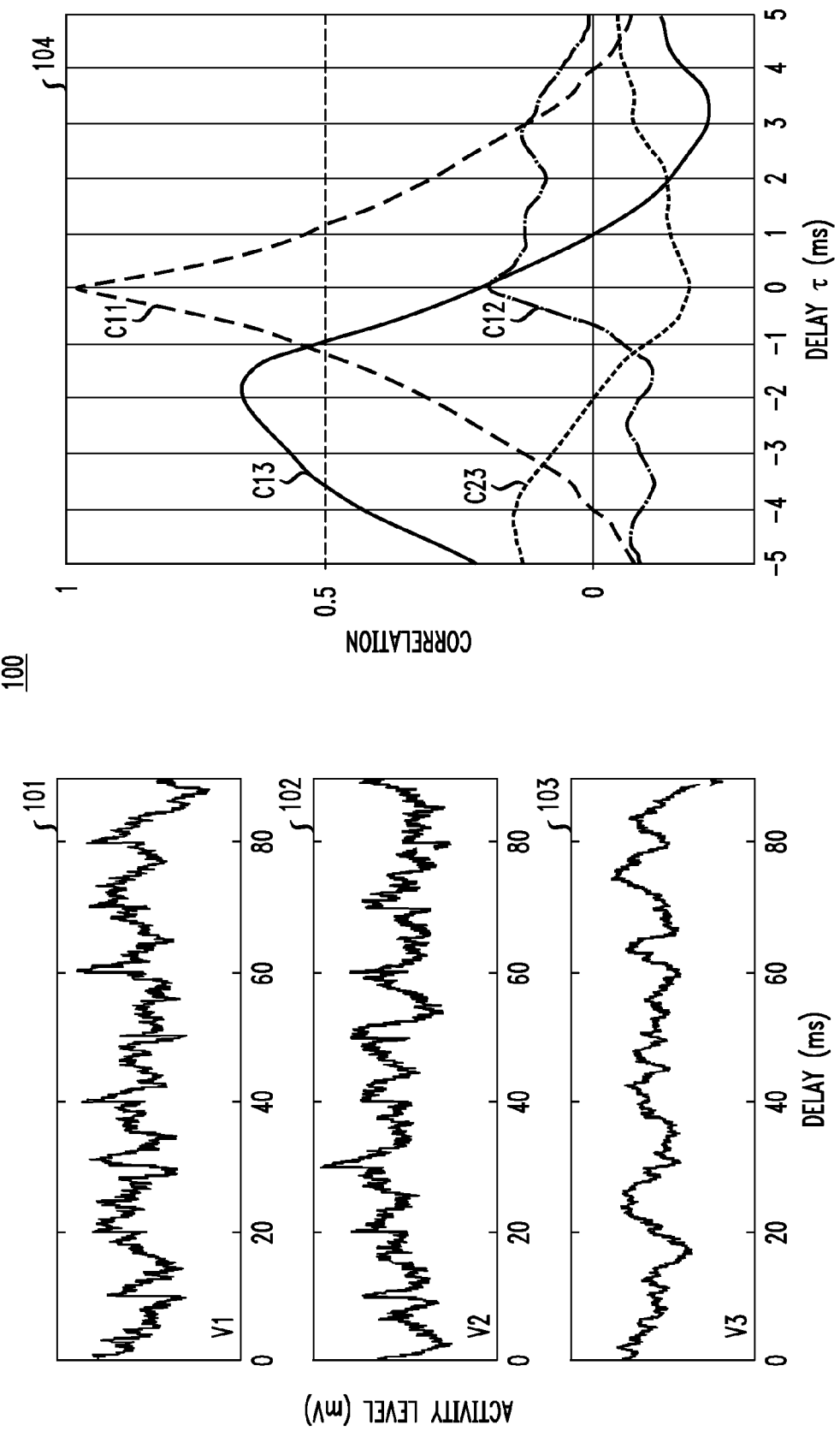
FIG. 1 shows graphs of time traces of activity for scanned voxel of the brain and a graph showing the results of a covariance or correlation analysis, according to an embodiment of the present invention.

Magnetic Resonance Imaging (MRI) is an imaging technique to visualize the internal structure and/or function of a body. MRI provides higher contrast between the different soft tissues of the body than provided by many other imaging techniques. Consequently, MRI is useful in neurology and brain imaging. MRI is also useful for imaging other portions of the body, for example, musculoskeletal, cardiovascular, and for oncological (cancer) imaging. MRI does not use ionizing radiation, but uses a powerful magnetic field to align the nuclear magnetization of, for example, hydrogen atoms in water in the body. Radio frequency (RF) fields are used to systematically alter the alignment of this magnetization, causing the hydrogen nuclei to produce a rotating magnetic field detectable by the scanner. This signal can be manipulated by additional magnetic fields to build up enough information to construct an image of the body or portions thereof.

Functional magnetic resonance imaging (fMRI) is a type of specialized MRI. fMRI, for example, measures the hemodynamic response (i.e., response to the dynamic regulation of the blood flow in the brain) related to neural activity in the brain or spinal cord of humans or other animals. Neurons require energy to function. This energy is supplied in the form of glucose and oxygen carried in hemoglobin. The blood supply of the brain is dynamically regulated to give active neural assemblies more energy while inactive neural assemblies receive less energy. Therefore, changes in blood flow and blood oxygenation in the brain (collectively known as hemodynamic) are closely linked to neural activity. When nerve cells are more active they consume more oxygen carried by hemoglobin in the red blood cells from local capillaries. The local hemodynamic response to this oxygen utilization is an increase in blood flow to regions of increased neural activity, occurring after a delay of, for example, 1-5 seconds. This local hemodynamic response may rise to a peak over, for example, 4-5 seconds before falling back to near baseline levels, leading to local changes in the relative concentration of oxyhemoglobin and deoxyhemoglobin and changes in local cerebral blood volume in addition to this change in local cerebral blood flow.

A voxel is a volume element, representing a value, a structure or a three-dimensional image on a three-dimensional grid. A voxel is analogous to a pixel, which represents two-dimensional image data. Voxels are frequently used in the visualization and analysis of medical and scientific data. As with a pixel, a voxel itself typically does not comprise spacial position or coordinates of the voxel. Rather, spacial position of a voxel is inferred based on the position of the voxel relative to other voxels (e.g., the position in the data structure that makes up a single volume image). The word voxel is a linguistic blend of the words volumetric and pixel.

A cycle of a network is a closed loop within the network, the loop comprising nodes and edges. A cycle comprises a sequence of connected edges starting and ending at a common node of the network, wherein edges (e.g., two edges) are considered connected to each other when the edges are connected to a common node. A specific node can only appear once in a cycle. Consideration of the direction of the edges of a cycle is not necessary to determine the existence of the cycle (e.g., a cycle does not have to be a feedback loop).

A feature of a network or portion thereof (e.g., a cycle in a network) is a prominent aspect or characteristic of the network or portion thereof. For example, magnetization, passthrough count and cycle compressibility are and describe features of the network or portions thereof. As described herein, features can be used, for example, for training and classification. Feature extraction relates to extracting, determining or obtaining features of the network or portions thereof.

Principles of the invention provide, for example, feature extraction from networks using topological measures of cycles, application of the feature extraction to classification processes, and discrimination between different subjects undergoing similar mental tasks or responding to similar stimuli. Principles of the invention further provide, for example, discrimination between different mental tasks carried out by a given subject. By way of example only, methods and techniques of the invention are adapted to identifying brain states, mental disease, schizophrenia, cognitive function, diagnostic states and/or Alzheimer's disease.

Embodiments of the invention are useful, for example, in characterizing large networks, such as large networks produced in analysis of functional magnetic resonance imaging (fMRI). fMRI measurements can give rise to large networks, for example, consisting of tens of thousands voxels or nodes, and edges. Conventional metrics to characterize large networks may not provide sufficient discrimination between different subjects or between different mental tasks carried out by a given subject.

Aspects of the invention are focused, for example, on specific measurements derived from cyclical motifs. A basic topological metric can be used as a proxy (e.g., to represent or to model) for the dynamical stability of a given network, and applied to the classification of brain states of subjects scanned with fMRI.

Embodiments of the invention, based on cyclical motifs, possess desired discrimination between subjects and between tasks that they perform. Metrics and measurements of the invention can be used to train a classification system to automatically perform discrimination between different subject classes and different task categories.

An aspect of the invention consists of a network comprising, or represented by, edges and nodes. Cycles of various lengths may be extracted from the network, for example by using a computer search algorithm. For each extracted cycle, measures of magnetization, cycle compressibility, the number of passthroughs and/or the net number of passthroughs may be computed.

The magnetization for a given cycle is defined as the absolute value of a difference between the number of edges oriented in a clockwise direction and the number of edges oriented in an anti-clockwise direction.

The cycle compressibility measures how much information is required to represent the sequence of edges in the cycle. For example, a measure of compressibility of a cycle includes how many numerical digits are required to represent a sequence of edges in the cycle. The numerical digits may be, for example, binary digits or bits.

A passthrough is defined as a node and a sequence of two edges coupled (e.g., connected) to the node, wherein at least one of the two edges is a directed edge, wherein at most one of the two edges is directed towards the node (incoming directed edge), and wherein at most one of the two edges is directed away from the node (outgoing directed edge). An undirected edge is neither incident upon nor exiting a node.

A passthrough can be considered a model of a portion of a network indicating a flow of the network into, out of, or through a node of the network. A directed passthrough may indicate a flow through the node. An undirected passthrough may indicate a flow into or out of the node, wherein there is a possibility of information flowing through the node. The flow may be, for example, a flow of information on a telecommunications network where the node is a telecommunications terminal, a flow of vehicles on a network of roads where the node is a city, or a flow of electrical impulses where the node is a region of the brain.

A passthrough may be a directed passthrough or an undirected passthrough. A directed passthrough is defined as a sequence of two identically directed edges (i.e., one edge directed to a node and the other edge directed from the same node, e.g., both edges parallel, directed to the right, and the node between the edges) coupled (e.g., connected) to a node. An undirected passthrough is defined to be a directed edge followed by an undirected edge (i.e., one edge directed to or away from a node and the other edge being an undirected edge coupled to the node), both edges coupled (e.g., connected) to the node. The passthrough includes the associated node and edges. The number of passthroughs and/or the net number of passthroughs can be counted for each cycle.

The three measures of magnetization, cycle compressibility and the number of passthroughs (or net number off passthroughs) may be computed over cycles of increasing cycle lengths. The three measures may be retained for the individual cycles, and/or averaged across all cycle lengths.

The three measures can be used as features in a classification task or scheme. The three measures can be used in isolation, in combination, with other features of the networks, and/or as properties of the nodes in the network. A classification regime is well suited to utilize the three measures. Pre-labeled class data can be used to train a classifier to distinguish between different subjects or different tasks. An embodiment of the invention is, for example, the combination of two or three of the cycle-related three measures with the framework of automatic classification and its application to distinguishing different fMRI-based scans.

Exemplary embodiments of the present invention are described herein with reference to the field of fMRI to illustrate and provide a specific domain for application of the disclosed techniques. However, embodiments of the invention are applicable to other fields where characterization of network topology is desired.

fMRI may be used to scan the brains of subjects while they perform mental tasks (stimuli) such as watching movies or pictures, listening to sounds, or playing a video-game. The time-series data collected at each voxel may contain enough information to predict the mental state of the subject, such as their emotion (e.g., happy, sad, or angry). However, information analyzed at the voxel level is insufficient to draw inferences about the evolution of correlated activity in different parts of the brain. It is desirable to have a representation of the brain activity that conforms to known biological properties of the brain, including established interconnections between specific brain regions, for example, the visual areas connection to the pre-frontal cortex.

To obtain such a brain activity representation, fMRI scans can be converted into graph-based representations of activity, where nodes, corresponding to different brain regions, are connected by edges if the activities of the corresponding brain regions are correlated. The edges can be directed if it is possible to establish causality (e.g., cause and effect), or are undirected. For example, for undirected edges no causality has been established. A procedure for conversion of fMRI data to a network is described as follows.

A functional network is determined by considering all functional voxels $\{v_i\}$ as possible nodes. The covariance ($c_{ij}$) of all functional voxels determines whether a binary functional link, or edge, exists between the voxels:

$$c_{ij} = \langle (v_i(t) - vo_i)(v_j(t) - vo_j) \rangle \sigma_i^{-1} \sigma_j^{-1},$$

where $vo_i = \langle v_i(t) \rangle_t$ and $\sigma_i^2 = \langle (v_i(t) - vo_i)^2 \rangle$, such that if the correlation between i and j exceeds a threshold, $C_T$, a functional link is considered, and none otherwise. That is:

if $c_{ij} > C_T$ then $d_{ij} = 1$, else $d_{ij} = 0$.

This approach can be extended to determine a possible directionality for the edge by considering the delayed or lagged covariance:

$$c_{ij}(\tau) = \langle (v_i(t+\tau) - vo_i)(v_j(t) - vo_j) \rangle \sigma_i^{-1} \sigma_j^{-1}.$$

The reason is that if there is a significant peak of the covariance between i and j at zero lag, then there is a potential binary symmetric link between them, as before. However, if the significant peak is not at zero lag, then it is considered that the preceding voxel, and only the preceding voxel, has a directed link pointing to the succeeding voxel. That is:

if $c_{ij}(\tau = 0) > C_T$ then $d_{ij} = d_{ji} = 1$;

else if $c_{ij}(\tau < 0) > C_T$ then $d_{ij} = 1$ and $d_{ji} = 0$;

else $d_{ij} = 0$.

The construction of a graph network from fMRI data is described below. FIG. 1 shows graphs of time traces of activity at each scanned voxel of the brain and a graph showing the results of a covariance or correlation analysis, according to an embodiment of the invention. Data measurements consist of time traces of activity at each scanned voxel of the brain, each time traces of activity is considered to be a time series. FIG. 1 shows time traces 101 for voxel 1 (i.e., V1), time trace 102 for voxel 2 (i.e., V2), and time trace 103 for voxel 3 (i.e., V3). For simplicity, only three time traces of three voxels are shown. It is understood, however, that many more time traces and correlations are possible. In this example, both V1 and V2 correspond to first and second brain regions driven by a common source, for example driven by a common structure or region of the brain, while V3 corresponds to a third brain region driven by the first brain region (corresponding to V1) with a delay. Graph 104 shows the results of a delayed covariance analysis, for example, by applying the above equations. Graph 104 is expressed as a normalized correlation, that is, the maximum possible correlation is indicated by "1" on the vertical axis. Graph 104 makes the lagged or time-shifted correlation between V1 and V3 evident, as shown by the curve C13. More specifically, the correlations (e.g., time-shifted correlations) of graph 104 have been computed for different values of the delay (i.e., $\tau$), shown on the x axis of graph 104. C13 represents the correlation between the time trace 101 for V1 and the time trace 103 for V3, where values of $\tau$ to the left of the origin correspond to the amount that time trace 103 for V3 is delayed from time trace 101 for V1 (e.g., from 0 to 5 ms delay indicated by −0 to −5) and values of $\tau$ to the right of the origin correspond to the amounts that time trace 103 for V3 is ahead of time trace 101 for V1 (e.g., from 0 to 5 ms delay indicated by 0 to 5). Similarly, C11, C12 and C23 represents the correlation between the time trace 101 with itself (i.e., time trace 101), time trace 101 with time trace 102, and time trace 102 with time trace 103, respectively. Similarly, for Cxy (x and y are indices with values 1, 2 or 3), values of $\tau$ to the left of the origin (negative values of $\tau$) correspond to the amount that the time trace for Vy is delayed from the time trace for Vx and values of $\tau$ to the right of the origin (positive values of $\tau$) correspond to the amounts that the time trace for Vy is ahead of time trace for Vx.

The correlation curve C13, indicate the correlation between time trace 101 for V1 and time trace 103 for V3 shows a significant peak at $\tau=-2$. That is, the maximum correlation between time traces 101 and 103 occurs when time trace 103 is delayed by 2 ms from time trace 101. The significance is computed by comparing the correlation value with a threshold (e.g., a predetermined threshold), which in this example is $C_T=0.5$. Alternate embodiments of the invention may use alternate values of the threshold $C_T$. As would be expected, curve C11 shows a correlation of unity at zero delay, that is, time trace 101 is self correlated with no delay. Only the curve C13 shows a significant peak at a nonzero value of $\tau$. Hence, we can assign a directional edge between a network node (N1) corresponding to V1 and another network node (N3) corresponding to V3. Because trace C13 shows the maximum correlation between V1 and V3 at a negative delay τ, indicating that V3 is delayed from V1, the direction of the directional edge is from node N1 to node N3. For example, a cause-effect relationship, with a cause related to voxel 1 and an effect related to voxel 2, is indicated by the time trace 101 for V1 time-shift correlated to time trace 103 for V3 after the corresponding data of the time trace 101 is advanced in time.

Even though such a network-based representation constitutes a compression of the original fMRI data, it is difficult to compare two such networks, either from a single subject performing multiple tasks or multiple subjects performing the same task. This is due, for example, to the high possible number of time traces and/or the high dimensionality of the related correlation graph, which could contain, for example, hundreds of nodes and thousands of edges. It is desirable to have the capability to compare two networks in order to design a classifier that can separate individuals performing the same task in order to identify subjects with specific mental diseases such as schizophrenia or Alzheimer's disease.

A given network may be converted to a graph-based representation that consists of nodes and edges. The nodes represent entities of interest, and the edges represent relationships between these entities. The edges may be directed or undirected. The topological structure of this network can be analyzed through the investigation of the types of basic patterns that exist within this network, known as network motifs. A cycle in the graph of the network is a special type of network motif. A method for characterizing the types of cycles present in the graph of the network or network is presented.

The method may consist of calculating the magnetization of cycles present in the network, for example, calculating the magnetization of cycles as a function of cycle length. The absolute magnetization of a cycle, termed |M|, is defined as the absolute value of the difference between the number of edges of a cycle that point in a clockwise direction of the cycle and the number of edges of the cycle that point in an anticlockwise direction of the cycle. The average of |M| over many cycles, indicated by <|M|>, is a network indicator of how many directed feedback loops are present in the network. A high <|M|> value indicates a network with a tendency to have more feedback loops when compared to a network having a smaller <|M|> value.

The method may consist of calculating a passthrough count. A passthrough count is, for example, the net number of passthroughs. FIGS. 2A-2G are node-edge diagrams illustrating how to calculate a passthrough count, termed H, which is based on the number of passthroughs, according to embodiments of the invention. In FIGS. 2A-2G, nodes 212 of a graph of a network are indicated by circles, directed edges of a graph of a network are indicated by arrow-headed lines and undirected edges 214 of a graph are indicated by lines any without arrowheads. Directed edges pointing toward nodes 212 are incoming directed edges 211. Directed edges pointing away from nodes 212 are outgoing directed edges 213. If one of two directed edges coupled or connected to a node 212 is incoming (e.g., incoming directed edge 211) and the other directed edge is outgoing (e.g., outgoing directed edge 213), a directed passthrough is present and the passthrough count H is incremented by one (H=H+1). This is illustrated by the directed passthroughs shown in FIGS. 2A and 2B. In this case, the directed passthrough comprises the node 212, the incoming directed edge 211 and the outgoing directed edge 213. Conversely, if two directed edges coupled to a node 212 are both incoming (e.g., incoming directed edges 211) or both outgoing (e.g., outgoing directed edges 213), a passthrough is not present and passthrough count H is decremented by one (H=H−1). The cases that are not passthroughs are shown in FIGS. 2C and 2D.

A directed passthrough comprises a node and an incoming directed edge (i.e., a directed edge incident to the node) connected to the node and an outgoing directed edge (i.e., a directed edge leaving the node) connected to the node. Alternately or additionally, as illustrated in FIGS. 2E and 2F, a passthrough may comprise a node, a directed edge (either an incoming directed edge 211 or outgoing directed edge 213) connected to the node, and an undirected edge 214 connected to the node. This type of passthrough is termed an undirected passthrough.

Figure 2A:
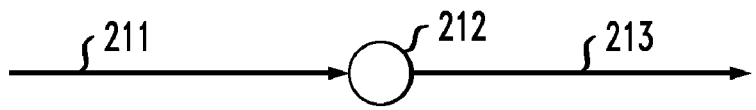
FIGS. 2A-2G are node-edge diagrams illustrating how to calculate a passthrough count based on the number of passthroughs, according to an embodiment of the present invention.
Figure 2B:
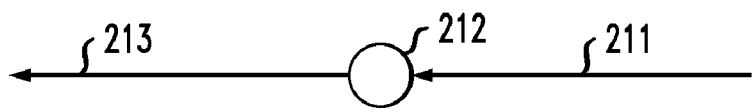
Figure 2C:
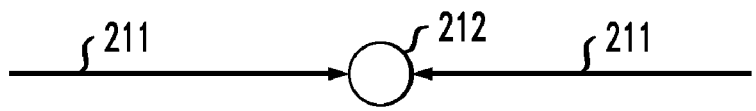
Figure 2D:
Figure 2E:
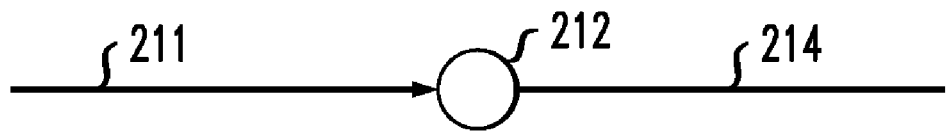
Figure 2F:
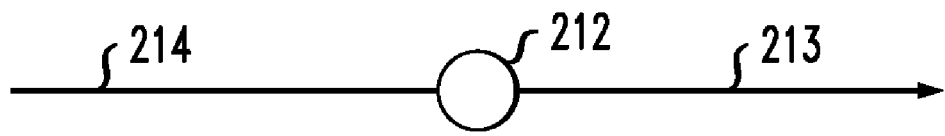
Figure 2G:

The arrangement of FIG. 2G, comprising a node connected to two undirected edges 214, is not a passthrough.

Note that the passthrough count H is the number of passthroughs considered minus the number of nodes considered that are not part of passthroughs. For example, if all nodes in a network, or portion thereof, are connected to two edges, the passthrough count for the corresponding network, or portion thereof, equals a difference between twice a total number of the passthroughs in the corresponding network, or portion thereof, and a total number of nodes in the corresponding network, or portion thereof.

Other networks may additionally include nodes connected to only one edge. The passthrough count for these networks is calculated in a similar way excepting that the nodes connected by only one edge would not be considered in the total number of nodes in calculating the passthrough count. Even if the edge connected to such a node is a directed edge, the node is not considered part of a passthrough.

Yet other networks may include nodes connected to more than two edges. In these networks, nodes that are connected to more than two edges are considered part of a passthrough if (i) at least one of the connected edges is a directed edge and (ii) all connected edges do not point in the same direction (i.e., all pointing to the node or all pointing away from the node) or if one of the connected edges is a undirected edge. In these networks, the passthrough count is calculated in a similar way as for a network comprising nodes connected to only two edges.

With regard to the passthrough count of FIGS. 2A-2G, a method for calculating the passthrough count is to (i) initialize the passthrough count to zero; (ii) for each node of the network, or portion thereof (e.g., a cycle portion of a network), increment the passthrough count if the node is part of a passthrough; and (iii) decrement the passthrough count if the node is not part of a passthrough.

For directed passthroughs, FIGS. 2A and 2B illustrate cases were the passthrough count H is incremented by one. For undirected passthroughs, FIGS. 2E and 2F illustrate cases were the passthrough count H is incremented by one. FIGS. 2C and 2D and 2G illustrate non-passthroughs where H is decremented by one. Because incoming edges 211 point in the opposite sense, with respect to node 212, than outgoing edges 213, incoming edges 211 are said to have opposite directionality with respect to outgoing edges 213.

As mentioned above, the passthrough count H may initially be set to zero. For every cycle of the network that we consider, the nodes of the cycle can have the configurations indicated in FIGS. 2A to 2G. For each node considered in a cycle, H is incremented or decremented as described above and in FIGS. 2A-2G. The resulting calculation of the passthrough count H for the cycle considers all the nodes in the cycle. In the same way, a passthrough count H can be obtained for all nodes in a network. If needed to distinguish a passthrough count for a cycle from a passthrough count for a network, a passthrough count for a cycle may be indicated by $H_C$ and a passthrough count for a network may be indicated by $H_N$. Herein, where it is otherwise clear that the passthrough count is a passthrough count for a cycle or a passthrough count for a network or could be either a passthrough count for a cycle of a network, the subscript may be dropped and the passthrough count simply indicated by H.

In the embodiment described above the passthrough count is incremented for both directed and undirected passthroughs. In an alternate embodiment, a passthrough count may be incremented only for directed passthroughs and either decremented for undirected passthroughs or neither incremented or decremented for undirected passthroughs. In another alternate embodiment, a passthrough count may be incremented only for undirected passthroughs and either decremented for directed passthroughs or neither incremented or decremented for directed passthroughs.

As an example, cycles comprising a feedback loop typically comprise many nodes having an incoming edge 211 and an outgoing edge 213. Therefore, such cycles tend to have a positive and possible large passthrough count. If a network has a large number of cycles with feedback loops then the passthrough count for the network will tend to be a large number. The passthrough count (H, $H_N$ or $H_N$) can be normalized by dividing the passthrough count by the number of edges encountered. The passthrough count can be considered to be a measure of the energy of a corresponding cycle or network.

The following is an example of application of passthroughs to a network of roads. A directed passthrough such as shown in FIG. 2A could indicate a flow (e.g., a flow of vehicles) into a node (e.g., Chicago) and leaving the node (e.g., Chicago).

The directed passthrough in FIG. 2E could indicate a flow of vehicles into Chicago but not indicate a flow of vehicles leaving Chicago. Another road connected to Chicago is indicated in FIG. 2E by the undirected edge, but traffic flow on the road is not indicated. However, the undirected edge could indicate a road that carries traffic out of or into Chicago, or indicate a road closed to traffic for repairs. The traffic on the road indicated by the undirected edge is unspecified.

In contrast, the structure, shown in FIG. 2C, is an example of a network structure that is not a passthrough. The structure is a node connected to two edges, each directed towards the node. The structure, for example, could indicate a flow of traffic into Chicago on each of two roads. For example, the two roads could connect Chicago to Los Angeles and New York. The structure of FIG. 2C does not indicate the possibility of traffic flow through Chicago because all traffic is indicated as flowing into Chicago.

In the above examples, the passthroughs indicate traffic flowing into, out of or through Chicago; the passthroughs either indicates or at least allow for the flow of traffic through Chicago; the directed passthroughs indicate traffic flowing through Chicago; and the undirected passthrough allows for traffic to flow through Chicago but does not specify that it does so. The structure that is not a passthrough does not indicate allowing for traffic to flow through Chicago.

Figure 3A:
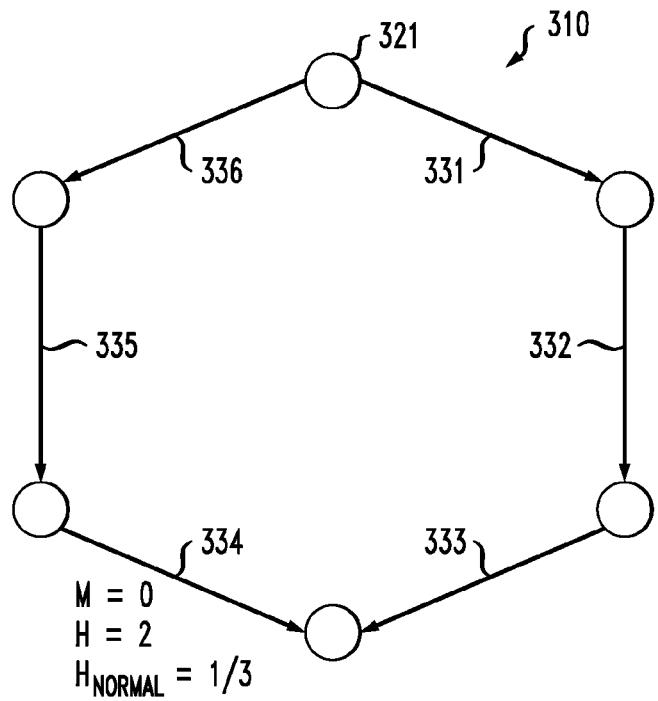
FIGS. 3A and 3B are exemplary network cycles and illustrate calculation of feedback indicators, according to an embodiment of the present invention.
Figure 3B:
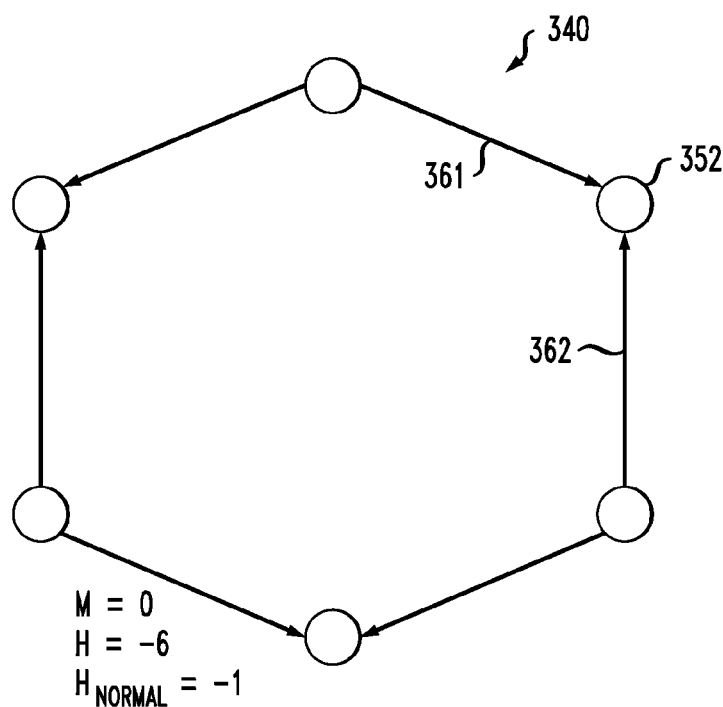

FIGS. 3A and 3B are exemplary cycles 310 and 340, respectively, according to embodiments of the invention. Summing H for the node of cycle 310 of FIG. 3A, a passthrough count H of 2 is calculated. The normalized passthrough count, $H_{Normal}$, equals H divided by the number of edges in the cycle. For cycle 310, $H_{Normal}=2/6=1/3$. For cycle 340 of FIG. 2B, H is calculated by the same method to equal −6, and $H_{Normal}=-6/6=-1$.

The magnetization |M| for cycle 310 is calculated by first initializing |M| equal to zero (|M|=0). Next start at a chosen node in the cycle, for example the first node 321. Consider a first edge 331, coupled to the first node 321. The first edge 331 points in a clockwise direction. Because the first edge 331 points in the clockwise direction increment |M| by one (|M|=|M|+1=0+1=1). Next consider the next sequential edge in the cycle, a second edge 332. The second edge also points in a clockwise direction, thus |M| is again incremented (|M|=1+1=2). After next considering a third sequential edge 333 pointing in a clockwise direction, |M|=3. After then considering a fourth sequential edge 334 that points in a counter-clockwise direction, |M| is decremented by one and then equals two (|M|=2). In this manner, following the fifth sequential edge 335, |M|=1, and following the sixth sequential edge 336, |M|=0. Calculation of |M| for the cycle is completed after considering all edges of the cycle. For cycle 310, the resultant |M| equals zero.

Calculation of the magnetization |M| for cycle 340, calculated by the same method used to calculate |M| for cycle 310, gives |M| for cycle 340 also equal to zero (|M|=0).

FIGS. 3A and 3B exemplify the advantage of using the two independent measures: (i) magnetization |M| and (ii) passthrough count H. For cycle 310, the magnetization |M| is zero because all the links summed around the entire loop cancel each other. For cycle 340, not only do all the links summed around the entire loop cancel each other, but magnetization equal to zero is achieved by canceling the links exactly at each node. That is, for |M|, the sum of two links coupled to a node is zero because one link is directed clockwise and one link is directed counter-clockwise. This is true for each and every directed link of cycle 340. For example, of the two directed links coupled to node 352 of cycle 340, one link 361 is directed clockwise and the other link 362 is directed counter-clockwise. Despite cycles 310 and 320 having the same magnetization |M|, the passthrough count H for cycles 310 is different than the passthrough count H for cycle 320.

In an exemplary application of networks and features of the invention to brains and fMRI, a node may correspond to a brain region and an edge may correspond to an interconnection between two different brain regions (two nodes). The interconnection may be indicated by a correlation of brain activity between the two different brain regions, for example, as indicated by correlation of fMRI data. A directed edge may correspond to an interconnection between two different brain regions where there is causality between the brain regions. For example, activity in a first brain region may cause or trigger activity in a second brain region. In this case, a directed edge directed from the first brain region towards the second brain region may indicate or model the interconnection, correlation and cause-effect relationship between the first and second brain regions. A first and a second node may indicate or model the first and second brain regions, respectively.

A feedback loop involving a number of interconnected brain regions may be indicated or modeled by a number of nodes interconnected by edges. An example is a sequence of four nodes N1, N2, N3 and N4 interconnected by edges E1, E2, E3 and E4, wherein E1 connects N1 and N2, E2 connects N2 and N3, E3 connects N3 and N4, and E4 connects N4 and N1, and wherein the edges are directed edges pointing in the same clockwise or counter-clockwise direction. For example, E1 is directed from N1 towards N2, E2 is directed from N2 towards N3, E3 is directed from N3 towards N4, and E4 is directed from N4 towards N1. Thus, there is a closed loop with a directed flow (e.g., a directed flow of information, material or cause-effect relationships) around the loop in one or the other direction of the loop. Note that each of the nodes is connected to one incoming directed edge (directed towards the node) and one outgoing directed edge (directed away from the node). Each node with the associated two directed edges is an example of a directed passthrough. For example, E4, N1 and E1, indicated by (E4, N1, E1), is a directed passthrough, as are (E1, N2, E2), (E2, N3, E3) and (E3, N4, E4). Thus, feedback loops of the brain, for example, can be indicated or modeled by cycles of a network wherein the cycles are comprised of directed passthroughs. Therefore, a passthrough count comprising a count of directed passthroughs can indicate, for example, the number or characteristics of feedback loops in the brain.

FIG. 4 illustrates a two-dimensional H-|M| feature plot 400, according to an embodiment of the invention. The magnetization |M| and passthrough count H are plotted. In place of H, $H_{Normal}$ may be plotted. The H-|M| feature plot 400 is constructed for multiple subjects from two classes, class A and class B. Squares 412 correspond to class A, and circles 411 correspond to class B. Subjects from both classes perform a mental task (stimuli), and corresponding fMRI activations (e.g., scans, time traces or time series) are obtained. From the fMRI activations, a network is constructed and H and |M| are calculated. H and |M| are plotted yielding the H-|M| distributions shown in feature plot 400.

It is then possible to use a classifier to determine a decision boundary 420, which distinguishes instances of class A (e.g., individuals of class A) from instances of class B (e.g., individuals of class B). An example of such a classifier is the support vector machine, which is described in the book: *The Nature of Statistical Learning Theory* by Vladimir Vapnik, Springer-Verlag publisher, 1995, ISBN 0-387-98780-0, the disclosures of which are incorporated herein by reference. Other classifiers, for example, rule-based classifiers which produce "if-then" rules may also be used. Such a rule-based classifier is described in the book: *C4.5: Programs for Machine Learning*, J. R. Quinlan, Morgan Kaufmann publishers, 1993, ISBN 1-55860-238-0, the disclosures of which are incorporated herein by reference. Different classifiers vary in their accuracy, generalizability and interpretability. The C4.5 rule-based classifiers provide rules that are easy to interpret; however, their performance may not be as good as support-vector machine based methods in terms of accuracy and generalizability. Practitioners of the art typically try out multiple classifiers for a given scenario, and select the one that gives the best performance. Though an embodiment of the present invention may use a support vector machine to learn the class boundaries, other classifiers can also be used in the spirit of the present invention.

FIG. 4 shows that network properties described by the features of cycles have sufficient discriminatory power to classify the subjects. A similar scheme can be used to distinguish different tasks, where the class labels are task-related, e.g. the squares correspond to Task 1 and the circles correspond to Task 2. For example, a scheme may discriminate between different mental tasks (stimuli) carried out by a given subject or a single group of subjects. The method associated with H-|M| feature plot 400 may be a low-dimensional space, and the features are easily interpretable, and the method can form the basis for designing classifiers to handle fMRI data for a variety of applications.

Note that the method associated with H-|M| feature plot 400 can be applied to a first group of subjects to determine a decision boundary 420 between class A and class B. This first group of subjects can be considered a learning or training group or set, wherein the decision boundary 420 is learned by applying methods of the invention. The training group may, for example, comprise multiple subjects from class A and the multiple subjects from class B receiving at least one common stimulus, or a single subject (or group of subjects) receiving two or more stimuli. The at least one stimulus or the stimuli may be, for example, performing mental tasks, sensory stimuli (e.g., visual, auditory, olfactory, tactile and taste), or direct stimulation (e.g., direct stimulation of the brain or nerves). The two or more stimuli may, for example, be received at different times and/or may be different mental tasks. Application of the stimulus or stimuli, measurement of the response and evaluation or classification of the response may be known as "evoked response."

Subsequently, one or more test subjects, experimental or diagnostic test subjects, can be analyzed according to methods of the invention to determine placement of each subject or the response of each subject to one of class A or class B based upon the position of the associated H-|M| coordinate with respect to the decision boundary 420. The one or more test subjects receive, for example, the same or similar stimulus (or stimuli) that the training group received.

For example, a test subject may be associated with class A or class B by obtaining for the test subject test subject measures each comprising the magnetization indicator, the passthrough count and/or the compressibility measure. After obtaining the measures, a relationship of the measures to the boundary is determined. The subject is then classified to class A or class B according to the determined relationship of the measures to the boundary.

If class A represent healthy subjects and class B represents subjects with an abnormality in cognitive function or a mental disease, then methods of the invention form the basis for providing information that can be used for diagnostic purposes.

An advantage of techniques of the invention, for example, is that methods of the invention can objectively produce relevant statistical information over many samples in a training set, objectively generalizing resultant learning, and objectively apply the resultant learning to a diagnostic set. This has advantage over direct human interpretation (e.g. subjective and/or biased interpretation) of all the data in the training set, followed by analysis (e.g. subjective and/or biased analysis) of a diagnostic case. However, since automatic classifiers may not be perfect, the diagnostic results provided by methods of the invention may be reviewed/modified by a human expert.

Figure 5:
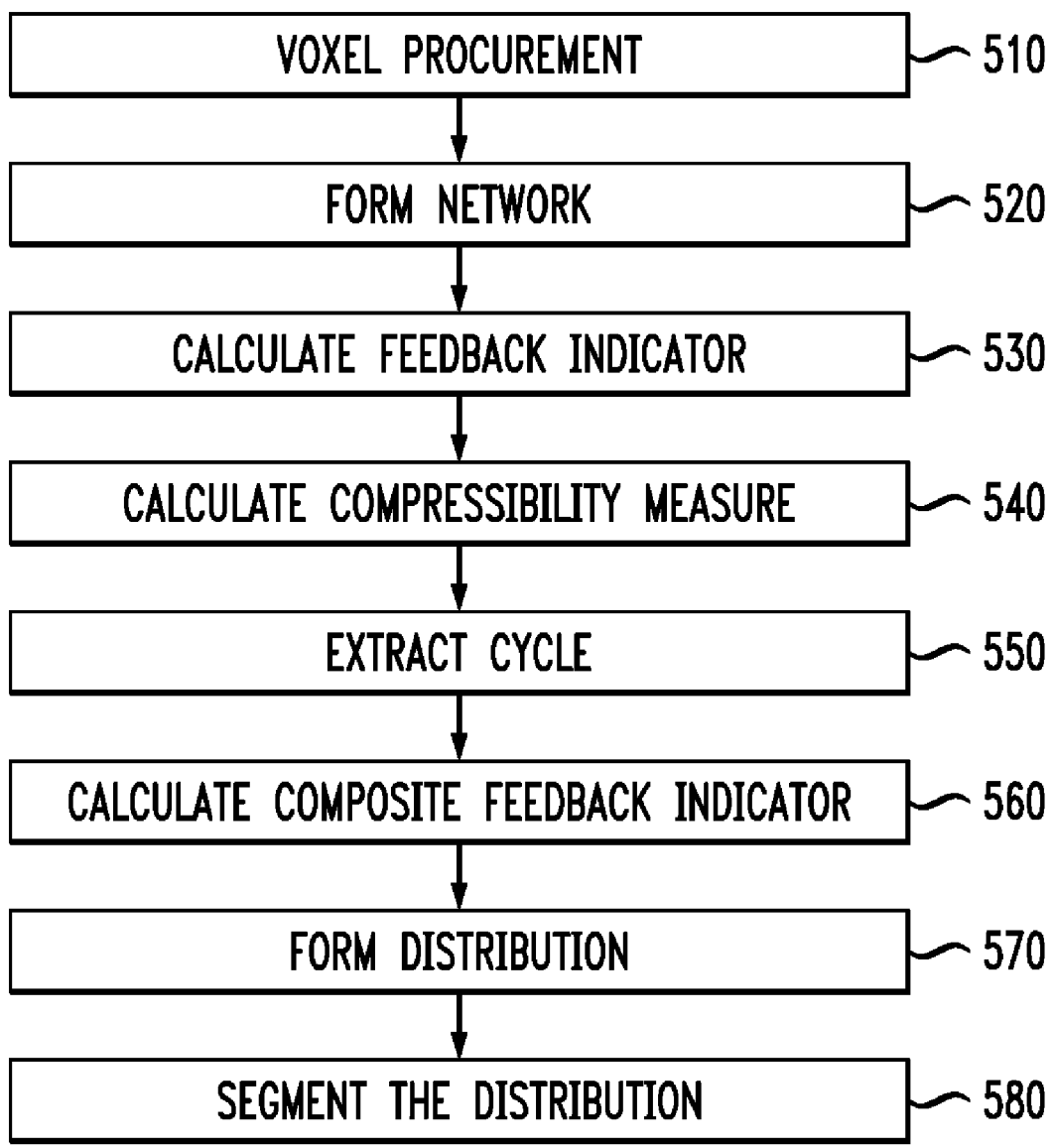
FIG. 5 is a flow diagram of a method of characterizing a network represented by a plurality of nodes and a plurality of edges, according to an embodiment of the present invention.

FIG. 5 is a flow diagram of a method 500 for characterizing a network represented by a plurality of nodes and a plurality of edges, according to an exemplary embodiment of the invention. The method 500 may be, for example, implemented on a processor (e.g. a processor device) coupled to a memory.

The first step 510 the method 500 comprises procuring or obtaining voxels. Each voxel comprises data. For example, voxels may be obtained by fMRI brain scanning and may contain time series data such as time traces 101, 102 and 103. For example, data of the voxels may be obtained by magnetic resonance imaging (e.g., fMRI) and corresponds to brain activities. Nodes of the network associated with the voxels may correspond to regions of the brain. Edges of the network associated with the voxels may correspond to interconnections among the regions of the brain.

The second step 520 comprises forming a network. The network represents or comprises the plurality of voxels. The network is represented by or comprises nodes and edges. Each of the nodes corresponds to at least one voxels and data of the at least one voxel. Example representations of networks or elements of networks are shown in FIGS. 2A-2G, 3A and 3B. Two nodes are coupled by an edge when corresponding data one of the nodes is correlated to corresponding data of the other node. An edge is a directed edge directed from one node to another node when there is a cause-effect relationship having a cause related to the one node and an effect related to the other node.

The third step 530 comprises calculating one or more feedback indicators. Calculations may be done, for example, by the processor coupled to the memory. Feedback indicators may be, for example, the magnetization indicator and/or the passthrough count. A feedback indicator is a type of network indicator. Network indicators may include other than feedback indicators, including the compressibility measure. Although in this embodiment, the magnetization indicator and the passthrough count are considered feedback indicators, in other embodiments the magnetization indicator and/or the passthrough count are not considered feedback indicators but are considered network indicators.

The fourth step 540 comprises calculating a compressibility measure, for example, a measure of the compressibility of a cycle. The compressibility measure comprising at least one measure of at least one amount of information required to represent at least one sequence of edges in at least one cycle. For example, the compressibility measure may include a numerical count of the number of numerical digits required to represent the at least one sequence of edges in at least one cycle. Execution of the fourth step 540 is optional.

The fifth step 550 comprises extracting one or more cycles from the network. For example, cycles of various lengths may be extracted from the network using a computer search algorithm. Feedback indicators may be extracted for each or multiples of the extracted cycles.

The sixth step 560 comprises calculating a composite feedback indicator, for example, by combining the calculated feedback indictors for each or multiples of the extracted cycle. Various methods may be used to combine the feedback indicators, for example, combining by calculating the average, median or mode of the calculated feedback indictors for each or multiples of the extracted cycle.

The seventh step 570 comprises forming a distribution of the feedback indicators. An exemplar distribution is the distribution, shown in FIG. 4, of magnetization M and passthrough count H. Other examples of two dimensional distributions are magnetization M and a compressibility measure or passthrough count H and a compressibility measure. Higher order dimension distributions are also contemplated, for example, a three dimensional distribution comprising magnetization M, passthrough count H and a compressibility measure.

The eighth step 580 comprises segmenting the distribution into a number of portions, separated by one or more boundaries, for example, segmenting a distribution into two portions separated by one boundary. An example is the segmentation of the distribution illustrated in FIG. 4, segmented into class A and class B by boundary 420.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring again to FIG. 5, which is a flow diagram or flowchart of the method 500, the flowchart and block diagrams in the Figure illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Accordingly, techniques of the invention, for example as depicted in FIGS. 1-5, can also include, as described herein, providing a system, wherein the system includes distinct software modules. By way of example only, the software modules may include: a voxel procurement module, a network forming module, a feedback indicator calculator module, a compressibility measure calculator module, a cycle extractor module a composite feedback indicator calculator module, a distribution forming module and a distribution segmentation module. The modules may be adapted, for example, to perform the steps of method 500 illustrated in FIG. 5.

Figure 6:
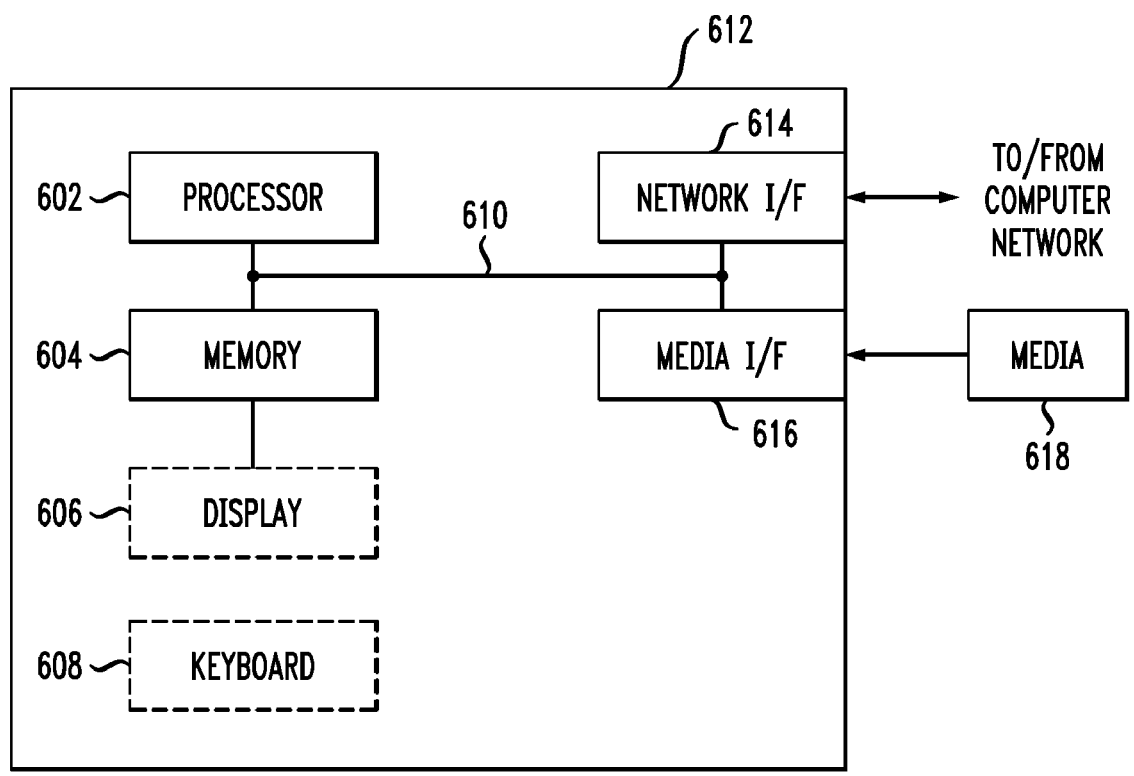
FIG. 6 depicts a computer system that may be useful in implementing one or more aspects and/or elements of the invention.

One or more embodiments can make use of software running on a general purpose computer or workstation. With reference to FIG. 6, such an implementation employs, for example, a processor 602, a memory 604, and an input/output interface formed, for example, by a display 606 and a keyboard 608. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, keyboard or mouse), and one or more mechanisms for providing results associated with the processing unit (for example, display or printer). The processor 602, memory 604, and input/output interface such as display 606 and keyboard 608 can be interconnected, for example, via bus 610 as part of a data processing unit 612. Suitable interconnections, for example via bus 610, can also be provided to a network interface 614, such as a network card, which can be provided to interface with a computer network, and to a media interface 616, such as a diskette or CD-ROM drive, which can be provided to interface with media 618.

A data processing system suitable for storing and/or executing program code can include at least one processor 602 coupled directly or indirectly to memory elements 604 through a system bus 610. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboard 608, display 606, pointing device, and the like) can be coupled to the system either directly (such as via bus 610) or through intervening I/O controllers (omitted for clarity).

Network adapters such as network interface 614 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 612 as shown in FIG. 6) running a server program. It will be understood that such a physical server may or may not include a display and keyboard.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method, implemented on a processor device, of characterizing a network represented by a plurality of nodes and a plurality of edges, the method comprising the step of:
  calculating, by the processor device, a passthrough count of at least a portion of the network;
  wherein the passthrough count comprises a count of a number of passthroughs in the at least a portion of the network, wherein a passthrough comprises:
    one of the plurality of nodes;
    a directed edge of the plurality of edges coupled to the one of the plurality of nodes; and
    another edge of the plurality of edges coupled to the one of the plurality of nodes;

wherein at most one of the directed edge and the other edge is directed towards the one of the plurality of nodes, and wherein at most one of the directed edge and the other edge is directed away from the one of the plurality of nodes.

2. The method of claim 1 further comprising the step of:
calculating, by the processor device, a magnetization indicator of a cycle of the network;
wherein the magnetization indicator comprises:
a count of a number of edges of the cycle that point in a clockwise direction of the cycle; and
a count of a number of edges of the cycle that point in a counter-clockwise direction of the cycle.

3. The method of claim 2, wherein the magnetization indicator equals a difference between a total number of edges of the cycle that point in the clockwise direction and a total number of edges of the cycle that point in the counter-clockwise direction.

4. The method of claim 1, wherein the passthrough count equals a difference between twice a total number of the passthroughs in the at least a portion of the network and a total number of nodes in the at least a portion of the network.

5. The method of claim 1, wherein the at least a portion of the network comprises a cycle of the network.

6. The method of claim 1 further comprising the step of:
calculating at least one compressibility measure of at least one cycle of the network;
wherein the compressibility measure comprising at least one of:
(i) at least one measure of at least one amount of information required to represent at least one sequence of edges in the at least one cycle; and
(ii) a numerical count of a number of numerical digits required to represent the at least one sequence of edges in the at least one cycle.

7. The method of claim 2 further comprising the step of:
extracting a plurality of cycles from the network;
wherein a network indicator is calculated for each extracted cycle; and
wherein the network indicator comprises at least one of the passthrough count and the magnetization indicator.

8. The method of claim 7, wherein the extracted cycles are of various cycle lengths.

9. The method of claim 7 further comprising the step of:
calculating a composite network indicator by combining the calculated network indictors for each extracted cycle.

10. The method of claim 9, wherein the composite network indicator is calculated by averaging the calculated network indictors for each extracted cycle.

11. The method of claim 9, wherein at least one of: (i) the magnetization indicator (ii) the passthrough count, and (iii) the composite network indicator is related to a number of feedback loops present in the network.

12. The method of claim 2, further comprising the steps of:
forming a distribution of at least two of: (i) the magnetization indicator, (ii) the passthrough count and (iii) a compressibility measure of the cycle, wherein the compressibility measure comprises a measure of an amount of information required to represent a sequence of edges in the cycle; and
segmenting the distribution into at least first and second portions separated by at least one boundary;
wherein, at least one of: (i) the first portion represents multiple subjects from a first class and the second portion represents multiple subjects from a second class, and (ii) the first portion represents at least one subject and a first stimulus, and the second portion represents the at least one subject and a second stimulus.

13. The method of claim 12, wherein the at least two of: (i) the magnetization indicator, (ii) the passthrough count and (iii) the compressibility measure are obtained from a training group comprising at least one of: (i) the multiple subjects from the first class and the multiple subjects from the second class, and (ii) the at least one subject;
wherein each of the multiple subjects from the first class and the multiple subjects from the second class receive a common stimulus; and
wherein the at least one subject receives the first stimulus at a first time and receives the second stimulus at a second time.

14. The method of claim 12 adapted to associate at least one test subject with one of the at least first and second portions by:
obtaining for the at least one test subject at least two test subject measures each comprising at least one of (i) the magnetization indicator, (ii) the passthrough count and (iii) the compressibility measure;
determining a relationship of the at least two test subject measures to the at least one boundary; and
classifying the at least one test subject according to the determined relationship.

15. The method of claim 1 further comprising the steps of:
obtaining a plurality of voxels, each of the plurality of voxels comprising data; and
forming the network, the network representing the plurality of voxels;
wherein each of the plurality of nodes corresponds to at least one of the plurality of voxels and data of the at least one of the plurality of voxels;
wherein a first node of the plurality of nodes and a second node of the plurality of nodes are coupled by one of the plurality of edges when corresponding data of the first node is correlated to corresponding data of the second node; and
wherein the one of the plurality of edges is a directed edge directed from the first node to the second node when there is a cause-effect relationship having a cause related to the first node and an effect related to the second node.

16. The method of claim 15, wherein the data of the plurality of voxels comprises time-dependent data, and wherein the cause-effect relationship is indicated by the corresponding data of the first node time-shift correlated to the corresponding data of the second node after the corresponding data of the first node is advanced in time.

17. The method of claim 15, wherein correlation between the corresponding data of the first node and the corresponding data of the second node is indicated when the correlation is above a predetermined threshold.

18. The method of claim 15, wherein the data of the plurality of voxels is obtained by magnetic resonance imaging and corresponds to activity of a brain, wherein the plurality of nodes correspond to a plurality of regions of the brain, and wherein the plurality of edges correspond to a plurality of interconnection among the plurality of regions of the brain.

19. The method of claim 1 adapted for identifying at least one of brain states, mental disease, schizophrenia, cognitive function, diagnostic states and Alzheimer's disease.

20. The method of claim 1, wherein the passthrough is one of: (i) a directed passthrough, and (ii) an undirected passthrough;
wherein the directed passthrough comprises one of the plurality of nodes, a directed edge of the network coupled to and directed towards the one of the plurality of nodes, and another directed edge of the network coupled to and directed away from the one of the plurality of nodes; and wherein the undirected passthrough comprises another one of the plurality of nodes, a directed edge of the network coupled to the other one of the plurality of nodes and an undirected edge of the network coupled to the other one of the plurality of nodes.

21. A method, implemented on a processor device, of characterizing a network represented by a plurality of nodes and a plurality of edges, the method comprising the step of:

calculating, by the processor device, a magnetization indicator of a cycle of the network;

wherein the magnetization indicator comprises:
a count of a number of edges of the cycle that point in a clockwise direction of the cycle; and
a count of a number of edges of the cycle that point in a counter-clockwise direction of the cycle.

22. A system for characterizing a network represented by a plurality of nodes and a plurality of edges, the system comprising:

a network indicator calculator module, implemented by at least one processor device, for calculating a passthrough count of at least a portion of the network;

wherein the passthrough count comprises a count of a number of passthroughs in the at least a portion of the network, wherein a passthrough comprises:
one of the plurality of nodes;
a directed edge of the plurality of edges coupled to the one of the plurality of nodes; and
another edge of the plurality of edges coupled to the one of the plurality of nodes;

wherein at most one of the directed edge and the other edge is directed towards the one of the plurality of nodes, and wherein at most one of the directed edge and the other edge is directed away from the one of the plurality of nodes.

23. The system of claim 22, wherein the network indicator calculator module is further adapted to calculate a magnetization indicator of a cycle of the network;

wherein the magnetization indicator comprises:
a count of a number of edges of the cycle that point in a clockwise direction of the cycle; and
a count of a number of edges of the cycle that point in a counter-clockwise direction of the cycle.

24. The system of claim 22 further comprising:

a compressibility measure calculator module, implemented by the at least one processor device, for calculating at least one compressibility measure of at least one cycle of the network;

wherein the compressibility measure comprising at least one of:
(i) at least one measure of at least one amount of information required to represent at least one sequence of edges in the at least one cycle; and
(ii) a numerical count of a number of numerical digits required to represent the at least one sequence of edges in the at least one cycle.

25. The system of claim 23 further comprising:

a cycle extractor module, implemented by the at least one processor device, for extracting a plurality of cycles from the network, wherein a network indicator is calculated for each extracted cycle, and wherein the network indicator comprises at least one of the passthrough count and the magnetization indicator; and a composite network indictor calculator module, implemented by the at least one processor device, for calculating a composite network indicator by combining the calculated network indictors for each extracted cycle.

26. The system of claim 23 further comprising:

a distribution forming module, implemented by the at least one processor device, for forming a distribution of at least two of: (i) the magnetization indicator, (ii) the passthrough count and (iii) a compressibility measure of the cycle, wherein the compressibility measure comprises a measure of an amount of information required to represent a sequence of edges in the cycle; and a segmentation module, implemented by the at least one processor device, for segmenting the distribution into at least first and second portions separated by at least one boundary;

wherein, at least one of: (i) the first portion represents multiple subjects from a first class and the second portion represents multiple subjects from a second class, and (ii) the first portion represents at least one subject and a first stimulus, and the second portion represents the at least one subject and a second stimulus.

27. The system of claim 22 further comprising:

a voxel procurement module, implemented by the at least one processor device, for obtaining a plurality of voxels, each of the plurality of voxels comprising data; and a network forming module, implemented by the at least one processor device, for forming the network, the network representing the plurality of voxels;

wherein each of the plurality of nodes corresponds to at least one of the plurality of voxels and data of the at least one of the plurality of voxels;

wherein a first node of the plurality of nodes and a second node of the plurality of nodes are coupled by one of the plurality of edges when corresponding data of the first node is correlated to corresponding data of the second node; and wherein the one of the plurality of edges is a directed edge directed from the first node to the second node when there is a cause-effect relationship having a cause related to the first node and an effect related to the second node.

28. Apparatus for characterizing a network represented by a plurality of nodes and a plurality of edges, the apparatus comprising:

a memory; and a processor device coupled to the memory, operative to:
calculate a passthrough count of at least a portion of the network;

wherein the passthrough count comprises a count of a number of passthroughs in the at least a portion of the network, wherein a passthrough comprises:
one of the plurality of nodes;
a directed edge of the plurality of edges coupled to the one of the plurality of nodes; and
another edge of the plurality of edges coupled to the one of the plurality of nodes;

wherein at most one of the directed edge and the other edge is directed towards the one of the plurality of nodes, and wherein at most one of the directed edge and the other edge is directed away from the one of the plurality of nodes.

29. A computer program product for characterizing a network represented by a plurality of nodes and a plurality of edges, the computer program product comprising a non-transitory computer readable storage medium having computer readable program code embodied therewith, the computer readable program code comprising computer readable program code configured to perform the step of:

calculating, by the processor device, a passthrough count of at least a portion of the network;

wherein the passthrough count comprises a count of a number of passthroughs in the at least a portion of the network, wherein a passthrough comprises:

one of the plurality of nodes;

a directed edge of the plurality of edges coupled to the one of the plurality of nodes; and another edge of the plurality of edges coupled to the one of the plurality of nodes;

wherein at most one of the directed edge and the other edge is directed towards the one of the plurality of nodes, and wherein at most one of the directed edge and the other edge is directed away from the one of the plurality of nodes.

* * * * *